United States Patent [19]

Archibald

[11] 4,061,758
[45] Dec. 6, 1977

[54] TREATING HYPERTENSION AND CENTRAL NERVOUS SYSTEM ABNORMALITIES

[75] Inventor: John Leheup Archibald, Windsor, England

[73] Assignee: John Wyeth & Brother Limited, Maidenhead, England

[21] Appl. No.: 771,591

[22] Filed: Feb. 24, 1977

Related U.S. Application Data

[63] Continuation-in-part of Ser. No. 569,242, April 18, 1975, Pat. No. 4,024,147, which is a continuation-in-part of Ser. No. 373,046, June 25, 1973, abandoned.

[30] Foreign Application Priority Data

June 30, 1972 United Kingdom .............. 30636/72

[51] Int. Cl.$^2$ .............................................. A61K 31/44
[52] U.S. Cl. ............................................................ 424/263
[58] Field of Search ......................................... 424/263

[56] References Cited

U.S. PATENT DOCUMENTS 3,527,761  9/1970  Archibald et al. .............. 260/293.77

3,907,810  9/1975  Cavalla et al. .................. 260/293.77

*Primary Examiner*—Stanley J. Friedman
*Attorney, Agent, or Firm*—Arthur E. Wilfond

[57] ABSTRACT

A group of heterocyclic compounds generally exhibiting central nervous system activity (such as depressant and anti-convulsant activities) and, in some cases, cardiovascular and/or anti-inflammatory activity are described. The compounds have the formula

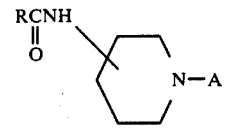

where A is an ethyl or propyl group which is monosubstituted by defined substituents or a di(loweralkyl) amino (loweralkoxy) carbonyl group and R is a phenyl group which may be substituted by defined substituents. Pharmaceutical compositions having hypotensive activity or central nervous system activity comprise a nontoxic carrier and an effective amount of such a compound.

3 Claims, No Drawings

TREATING HYPERTENSION AND CENTRAL NERVOUS SYSTEM ABNORMALITIES

This application is a continuation-in-part of Application Ser. No. 569,242 filed Apr. 18, 1975 now U.S. Pat. No. 4,024,147. Application Ser. No. 569,242 in turn is a continuation-in-part of now abandoned application Ser. No. 373,046 filed June 25, 1973.

The present invention concerns piperidines useful pharmacologically, in particular, exhibiting central nervous system activity and, in some cases, hypotensive active. The invention provides pharmaceutical compositions containing the piperidine compounds.

The invention presents pharmaceutical compositions having hypotensive activity or central nervous system activity comprising a non-toxic carrier and a compound selected from those of the formula

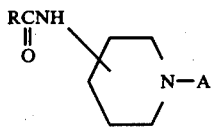
(I)

and their pharmaceutically acceptable acid addition salts, wherein A represents a member selected from the class consisting of
i. alkyl containing 2 to 3 carbon atoms mono-substituted by a substituent selected from hydroxyl, di(lower alkyl)amino, cyano, halogen, groups of the formula -CO.NX.Y where X and Y are selected from hydrogen and lower alkyl, groups of the formula -CO. T where T is lower alkyl, the semicarbazone and phenyl hydrazone derivatives of said groups of the formula -CO.T, (lower alkoxy)carbonyl and groups of the formula -N(CH$_2$R$^1$)R$^2$ where R$^1$ is selected from phenyl, monohalophenyl, mono(lower alkyl)-phenyl and mono(lower alkoxy) phenyl and R$^2$ is pyridyl; and
ii. di(lower alkyl)amino(lower alkoxy) carbonyl; and
R represents a member selected from the class consisting of phenyl and phenyl substituted by one to two substituents selected from lower alkyl, halogen, and nitro.

The term "lower" as applied to a radical or group denotes that the radical or group contains up to 6 carbon atoms, preferably up to 4 carbon atoms. As lower alkyl groups there may be mentioned, for instance, methyl, ethyl, n-propyl, i-propyl, n-butyl and n-hexyl. As lower alkoxy groups there may be mentioned, for example, methoxy, ethoxy, propoxy, butoxy and hexoxy.

A first preferred subgenus of the invention consists of the cases where A is alkyl containing 2 to 3 carbon atoms mono-substituted by groups of the formula -N(CH$_2$R$^1$)R$^2$ where R$^1$ and R$^2$ are as defined above or by the phenylhydrazone derivative of the groups having formula -CO.T where T is as defined above. The preferred substituent is the groups of formula -N(CH$_2$R$^1$)R$^2$. R$^1$ may represent, for example, phenyl, chlorophenyl, bromophenyl, tolyl, ethylphenyl, methoxyphenyl or ethoxyphenyl. R$^1$ preferably represents mono(loweralkoxy)phenyl, preferably methoxyphenyl. R$^2$ represents pyridyl, preferably 2-pyridyl.

The group A may also represent alkyl containing 2 to 3 carbon atoms mono-substituted by hydroxyl, di(lower alkyl)-amino, preferably di(ethyl)amino, cyano, halogen, particularly fluorine, chlorine, bromine and iodine, groups of the formula -CO.NX.Y where X and Y are selected from hydrogen and lower alkyl, for instance -CONH$_2$, and (lower alkoxy)carbonyl, preferably methoxycarbonyl.

The aforesaid alkyl containing 2 to 3 carbon atoms is ethyl or propyl, preferably ethyl.

The group A may also represent di(lower alkyl)amino(lower alkoxy)carbonyl, preferably (diethylamino)ethoxycarbonyl.

As illustrative examples of A there may be particularly mentioned those of the formulae

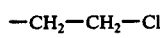

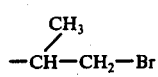

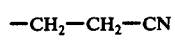

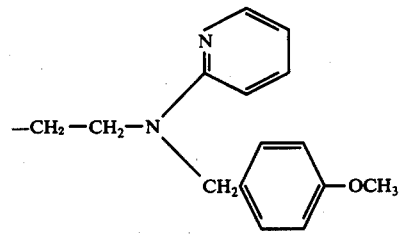

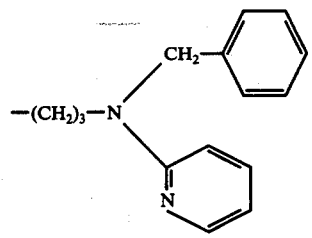

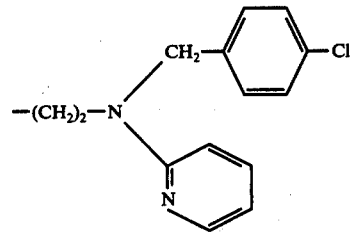

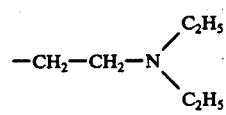

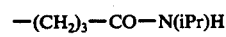

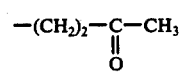

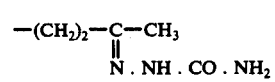

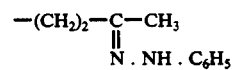

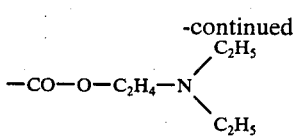

A second preferred subgenus of the invention resides in the compounds where R is phenyl. In this case A is preferably as defined in connection with the first preferred subgenus.

R may also represent phenyl substituted with one to two substituents independently selected from lower alkyl, for instance, methyl, ethyl, propyl or butyl, halogen, particularly fluorine, chlorine, bromine or iodine, and nitro. Examples of R include phenyl, tolyl, dichlorophenyl and nitrophenyl.

Examples of pharmaceutically acceptable acid addition salts are those formed from inorganic and organic acids, in particular such salts as the sulphate, hydrochloride, hydrobromide, hydroiodide, nitrate, phosphate, sulphonates (such as the methane-sulphonate and p-toluene-sulphonate), acetate, maleate, fumarate, tartrate and formate.

Some of the compounds of formula (i) are useful as intermediates for the preparation of other compounds by reactions that modify the group A or R. The compounds of general formula (I) exhibit pharmacological activity, for instance, they generally exhibit central nervous system activity (such as depressant or anti-convulsant activities) and some compounds also have action on the cardiovascular system (such as hypotensive activity) and/or anti-inflammatory activity when tested on warm-blooded animals.

The compounds having formula I and their pharmacologically acceptable acid addition salts are tested for central nervous system by administration of the compound to mice. They exhibit depressant activity in such a test at doses varying from compound to compound. In general the active doses are in the range from 40 to 400 milligrams per kilogram of body weight administered orally or intraperitoneally. Compounds can be tested for cardiovascular activity by the following procedure:

Charles River rats of 200 to 250 grams body weight are anaesthetised with pentobarbitone-sodium (60mg/kg i.p) The animals are allowed to breathe spontaneously through tracheostomy tubes. Carotid arterial blood pressure is monitored and recorded. The drug is administered via a catheter inserted in the jugular vein. Control measurement of blood pressure is taken immediately prior to, and 30 seconds and 15 minutes following, the injection of a dose of the test compound. The method is carried out in duplicate. Compounds are regarded as producing hypotension if they produce a 30 mm. Hg or more fall in diastolic blood pressure.

In particular, the end products of Examples 2, 4, 10 and 11 are active in producing hypotension. Active doses vary from compound to compound but were generally within the range of 3.2 to 25.6 milligrams per kilogram of body weight. Compounds where the substituent is at the 4-position, i.e., of formula

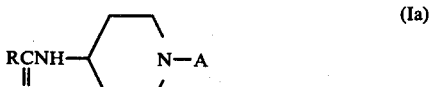

are preferred.

The new compounds of the invention may be prepared by building up the molecule by processes known per se. Thus, for example, the acyl group RCO- can be introduced by standard acylation procedures. A substituted alkyl group represented by A can be introduced by alkylation. A di(lower alkyl)amino(lower alkoxy)-carbonyl group represented by A can be introduced by initial introduction of a -CO-Cl group and subsequent reaction with di(lower alkyl)amino(lower)alkanol. The piperidine ring can be obtained by reduction of a pyridine ring.

The present invention provides a process for preparation of compounds of formula I and their salts, in which
a. a compound of formula

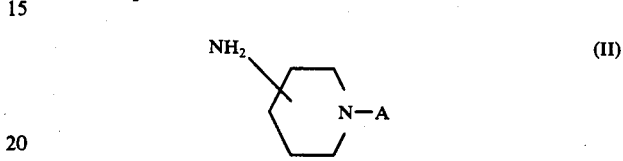

(where A is as defined above) or an activated amino derivative thereof is coupled with an acid of formula RCO₂H (where R is as defined above) or a reactive derivative thereof, or b. a compound of formula

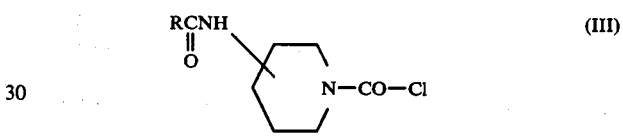

(where R is as defined above) is reacted with di(lower alkyl)amino(lower)alkanol; or c. a compound of formula

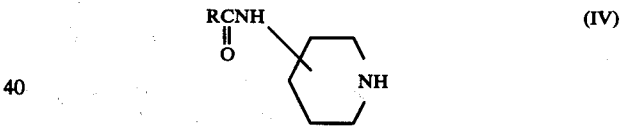

or an acid addition salt thereof is reacted with an alkylating agent of formula A-Z where Z is a leaving group or atom and A is as defined above in connection with formula I or with an agent that introduces a substituted alkyl group A by an addition reaction; or d. a compound containing the ion

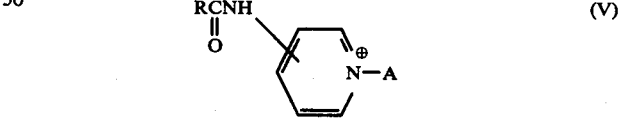

where R and A are as defined above is reduced, or e. a compound of formula

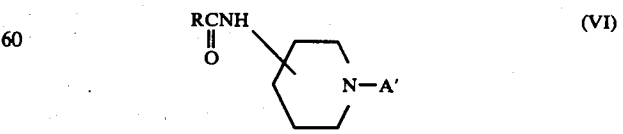

where R is as defined above and A' is alkyl of 2 to 3 carbon atoms monosubstituted by carboxyl or a derivative thereof or its acid addition salt is amidated to produce the compound where A is alkyl of 2 to 3 carbon atoms monosubstituted by the substituted or unsubstituted carbamoyl group

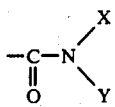

where X and Y are selected from hydrogen and lower alkyl. The process may further include a step in which a compound of formula I or an acid addition salt thereof is converted to a further compound and if desired a compound of formula I is converted into an acid addition salt thereof or an acid addition salt is converted into a compound of formula I.

Compounds of the invention may be prepared by introduction of the RCO- acyl groups by standard coupling methods [see, for example, "The Chemistry of The Amino Acids" by Greenstein and Winitz (John Wiley & Sons, Inc.)]. Acyl groups can be introduced by direct reaction of a carboxylic acid with the amino group in the presence of a functionalising or dehydrating agent. The acid may instead be reacted with an activated amino derivative of the compound of formula II. Acyl groups may also be introduced by reaction of the compound of formula II with an acylating derivative of the acid RCOOH. As acylating derivatives there may be mentioned the carboxylic acid halides, preferably the acyl chloride, the simple or mixed anhydrides of the acid, active esters and azides.

Where it is desired to obtain final products containing a functional group susceptible to acylation the starting material used may contain a chemically protected form of the group or an appropriate precursor from which the function may be subsequently generated. Thus, for example, a free hydroxy group may be generated by removing a chemical blocking group or by reduction of a carbonyl group. Phenylhydrazones and semicarbazones may be obtained by reaction of the corresponding ketone with phenylhydrazine or semicarbazide.

The compounds of the invention may also be prepared by reacting a compound of formula

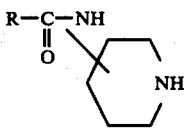

with an alkylating agent of formula A-Z where Z is a leaving group or atom and A is substituted ethyl or propyl. As examples of such alkylating agents there may be mentioned substituted ethyl or propyl halides for example, the chlorides or bromides.

Certain classes of substituted alkyl groups A may be introduced by addition reactions. Thus, for example, compounds where A represents a β-hydroxy alkyl group may be made by reacting an epoxide such as ethylene oxide or propylene oxide with the compound of formula (IV). Moreover β-oxoalkyl groups may be introduced by reacting the compound of formula IV with an α, β-unsaturated ketone The following are examples of such reactions:

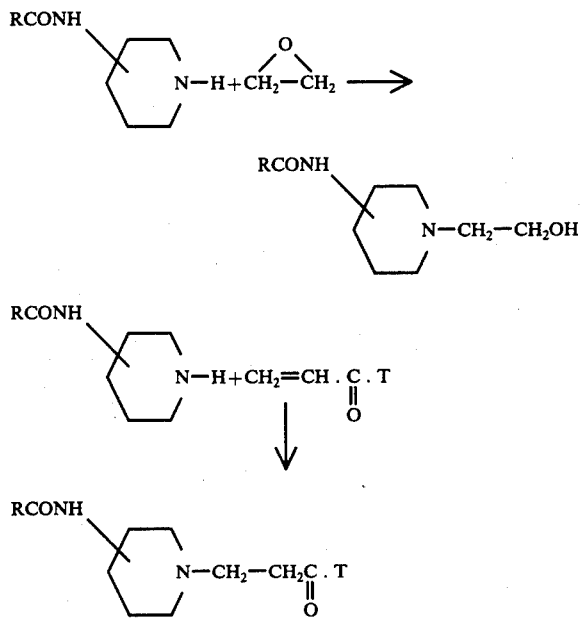

where T is a lower alkyl group.

Compounds of the invention may also be prepared by reacting a compound of formula (IV) with phasgene to form compounds of the formula

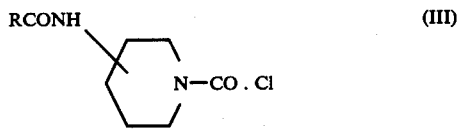

and subsequent reaction with a di(lower alkyl)amino(-lower)alkanol

The piperidine ring in the compounds of the invention may be introduced by reduction of a corresponding compound with a pyridine ring. The reduction may be effected by catalytic hydrogenation or a hydride transfer agent for example, an alkali metal borohydride. In such methods a reducible function in A may be reduced, for example, compounds where A is an oxo-alkyl group may be reduced to a hydroxy-substituted alkyl group A.

Once a compound of general formula (I) has been prepared, then if necessary or desired one or more substituents in the molecule may be converted to another substituent each within its own meanings specified in connection with formula (I).

For example if a compound of formula (I) is prepared in which the chain A contains a carbonyl function, then this chain may be reduced. For example, a keto-alkyl group may be reduced to form a free hydroxy group with an alkali metal borohydride. A hydroxy alkyl group A may be converted into a haloalkyl group in known manner. A cyanoalkyl group A may be hydrolysed to form alkyl substituted by carbamoyl. A haloalkyl group A may be converted into a substituted or unsubstituted aminoalkyl group A in known manner.

The invention also provides a process for the preparation of the new compounds of formula I and their acid addition salts where A represents the alkyl group monosubstituted by a carbamoyl group of formula

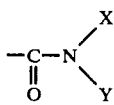

where X and Y are selected from hydrogen and lower alkyl, wherein a corresponding compound where A represents the alkyl group mono-substituted by carboxyl or a derivative thereof, for instance, lower alkoxycarbonyl, is amidated.

In order to prepare a compound of general formula (I) in which A represents a phenylhydrazone or semicarbazone of an oxo-alkyl radical, the corresponding ketone is converted into the desired derivative by methods known in the literature. In this respect reference may be made to (I) Reagents for Organic Synthesis by L. Fieser and M. Fieser (John Wiley & Sons, Inc., 1967) at page 434 and 479; (2) U.K. Patent Specification No. 1,223,491; and (3) A Scheme of Qualitative Organic Analysis by F. J. Smith and E. Jones (Blackie & Son Ltd., 1960) at page 38.

The starting material for the above mentioned processes for the preparation of the new compounds of the invention are accessible by known methods or, in certain cases, known per se.

The invention further includes pharmaceutical compositions containing as active ingredients a compound of formula (I) or a pharmaceutically acceptable acid addition salt thereof which may be micronised if desired. In addition to the active ingredient, said composition also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilized by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The following non-limiting Examples illustrate the invention:

EXAMPLE 1

1-(2-Chloroethyl)-4-benzamidopiperidine a. A mixture of 2.04 grams (0.01 mole) of 4-benzamidopiperidine, 1.25 grams (1 equivalent) of 2-bromoethanol and 2.76 grams (4 equivalents) of potassium carbonate were stirred at 100° C in 2 milliliters of methyl etyl ketone for 2 hours. The mixture was filtered hot and the inorganic residue was washed well with hot methyl ethyl ketone. The filtrate was evaporated to dryness and the resulting white solid recrystallised from ethyl acetate to give 1.55 grams (62%) of 1-(2-hydroxyethyl)-4-benzamidopiperidine.

b. 1 Gram of 1-(2-hydroxyethyl)-4-benzamidopiperidine suspended in 2 milliliters of dry benzene was treated with 0.62 gram of thionyl chloride. The stirred mixture was refluxed for 3 hours., then cooled and filtered to give the title compound as a light grey solid. Crystallisation from ethanol-ether of this hydrochloride gave 0.8 grams (62%) of pale yellow needles, melting point 238.5° C.

Analysis: $C_{14}H_{19}ClN_2O \cdot HCl$ requires C, 55.45%; H, 6.65% N, 9.24%. Found: C, 55.42%; H, 6.85%; N, 9.29%.

EXAMPLE 2

4-Benzamido-1-(3-oxobutyl)piperidine 8.16 Grams of 4-benzamidopiperidine were dissolved in 60 milliliters of ethanol containing 4.68 grams of methyl vinyl ketone. The solution was stirred at room temperature for 3 hours then left overnight. On making the solution acid with ethanolic HCl 9.92 grams (80% yield) of the product as its hydrochloride crystallised out. Recrystallisation from ethanol gave the pure title compound hydrochloride as colourless needles, m.p. 308°–310° C.

Analysis: Found, C, 61.54%; N, 7.53%; N, 9.13%. $C_{16}N_{22}N_2O_2 \cdot HCl$ requires C, 61.82%; H, 7.46%; N, 9.01%).

EXAMPLE 3

4-Benzamido-1-(3-semicarbazonobutyl)piperidine 6.22 Grams of the product of Example 2, semicarbazide hydrochloride (2.24 g.) and ammonium acetate (4.8 g.) were dissolved in water (40 ml.) and kept at room temperature for 1 hour. The product which crystallised out was collected and dried to give the title compound hydrochloride, quarter hydrate (5.05 g), melting point 155–156°.

(Analysis: Found, C, 54.96%; H, 7.27%; N, 18.99%. $C_{17}H_{25}N_5O_2 \cdot HCl \cdot 1/4H_2O$ requires C, 54.82%; H, 7.25%; N, 18.81%).

EXAMPLE 4

4-Benzamido-1-(3-phenylhydrazonobutyl)piperidine

The title compound was obtained as a hydrochloride, sesquihydrate, melting point 168°–170° C, by following the procedure of the foregoing example but using phenylhydrazine hydrochloride in place of semicarbazide hydrochloride.

(Analysis: Found, C, 62.09%; H, 7.42%; H, 13.23%. $C_{22}H_{28}N_4O \cdot HCl \cdot 1\frac{1}{2}H_2O$ requires C, 61.75%; H, 7.53%; N, 13.10%).

EXAMPLE 5

4-Benzamido-1-(2-diethylaminoethyl)piperidine

Equimolar amounts of 2-diethylaminoethyl chloride, hydrochloride and 4-benzamidopiperidine were stirred under reflux in isopropanol with 2.5 molar equivalents of anhydrous potassium carbonate for 18 hours. The hot suspension was filtered and the filtrate was treated with ethereal HCl to give the title compound as a dihydrochloride, hemihydrate, m.p. >220° (with decomp.)

(Analysis: Found: C, 56.67%; H, 8.42%; N, 10.82%; $C_{18}H_{29}N_3O2HCl \cdot 1/2H_2O$ requires C, 56.09%; H, 8.37%; N, 10.90%).

EXAMPLE 6

β-(Diethylamino)ethyl-4-benzamidopiperidine-1-carboxylate a. 4-Benzamidopiperidine-1-carbonyl chloride Phosgene was bubbled into dry toluene (75 ml) until 3.71 g. (0.0375 mole) had dissolved. To this solution was added a suspension of 4-benzamidopiperidine (5 g., 0.025 mole) in dry toluene (120 ml). The mixture was heated under reflux for one hour and the solvent was evaporated to give a residue of the title compound (5g., 75%).

b. Sodium (0.432 g., 0.0188 mole) was added to β-diethylaminoethanol (2.23 g., 0.0190 mole) in dry toluene (80 ml) and the mixture was refluxed to give a complete solution. 4-Benzamidopiperidine-1-carbonyl chloride (4.2 g., 0.01575 mole) in suspension in dry toluene (150 ml.) was added in portions and the mixture refluxed for 2½ hours. Water was added to the mixture, the toluene layer was collected, dried and evaporated to give the title compound (3.27 g. 37%), melting point 78°–82° C.

Analysis: $C_{19}H_{29}N_3O_3$ requires C, 65.67%; H, 8.41%; N, 12.09%. Found: C, 65.38%; H, 8.26%; N, 11.87%.

EXAMPLE 7 a.
4-Benzamido-1-(3-methoxycarbonylpropyl)piperidine

An intimate mixture of 4-benzamidopiperidine (2.0g.), methyl 4-bromobutyrate (2.0g.) and potassium carbonate (1.5 g.) was stirred and heated on a steam bath for 15 minutes. An exothermic reaction occurred and the semi-molten mixture set solid. Trituration with water (20 ml.) and filtration provided the title compound (2.41 g., 82%), m.p. 116° (Found: C, 67.10; H, 8.00; N, 9.39; $C_{17}H_{24}N_2O_3$ requires C, 67.08; H, 7.95; N, 9.20%).

b. 4-Benzamido-1-(3-carbamoylpropyl)piperidine

4-Benzamido-1-(3-methoxycarbonylpropyl)piperidine (5.0g). in .880 ammonia solution (50 ml.) was heated in a sealed tube at 105° for 18 hours. The tube was cooled and opened and the resulting crystals were collected and dried to give the title compound (2.53 g.) m.p. 199° C.

(Analysis: Found: 66.56%; H, 8.04%; N, 14.30%. $C_{16}H_{23}N_3O_2$ requires C, 66.41%; H, 8.01%; N, 14.52%).

EXAMPLE 8

4-Benzamidopiperidino)butyric acid isopropyl amide

A mixture of 4-benzamidopiperidine (2.0g.),4-chloro-N-isopropylbutyramide (1.8g.) and potassium carbonate (1.5g.) was finely ground and heated with stirring on a steam bath for 10 minutes. Trituration with water and filtration gave a solid (1.64 g.) which was dissolved in ethanolic HCl and diluted with ethyl acetate to give the crude product hydrochloride. Recrystallisation from acetonitrile/ether/ethyl acetate/methanol provided the title compound hydrochloride, quaterhydrate, m.p. 217° C. (Found: C, 61.18; H, 7.94; N, 10.96. $C_{19}H_{29}N_3O_2 \cdot HCl \cdot 1/4H_2O$ requires C, 61.27; H, 8.25; N, 11.28%).

EXAMPLE 9

4-Benzamido-1-(3-cyanopropyl)piperidine

Prepared in the same way as Example 7 (a) but using 4-chlorobutyronitrile as the alkylating agent, the title compound melted at 237° C (Found: C, 62.66%; H, 7.25%; N, 13.52%. $C_{16}H_{21}N_3O$ requires C, 62.42%; H, 7.21%; N, 13.65%).

EXAMPLE 10

1-(2-hydroxyethyl)-4-benzamidopiperidine 20.43 Grams (0.1 mole) of 4-benzamidopiperidine, 15.0 grams (20% excess) of 2-bromoethanol, 27.6 grams (0.2 mole) of potassium carbonate and 20 milliliters of methyl ethyl ketone were heated and stirred at 100° C for 2 hours. The mixture was filtered hot to remove inorganic material and the filtrate was evaporated to give 14.34 grams of a white solid which was recrystallised from ethyl acetate to give 13.56 grams of the title compound. Yield: 54.6%. Melting point: 133.3° C. The hydrochloride (melting point 189.1° C) was obtained by dissolving the base in ethanolic hydrogen chloride and adding ether to induce crystallisation. Analysis: $C_{14}H_{20}N_2O_2 \cdot HCl$ requires C, 59.05%; H, 7.43%; N, 9.84%. Found: C, 59.28%; H, 7.58%; N, 9.67%.

EXAMPLE 11

4-Benzamido-1-(2-[N-(p-methoxybenzyl)-N-(2-pyridyl)]-amino)ethylpiperidine

To 50 ml. of liquid ammonia was added 89 milligrams of lithium wire in portions followed after first addition by a few crystals of ferric nitrate. When the initial blue colour had disappeared and the lithium had all dissolved the ammonia was allowed to evaporate. To the solid lithium amide was allowed to evaporate. To the solid lithium amide was added 2-[p-methoxybenzyl]-aminopyridine (928 mg., 0.0043 mole) in 50 ml. dry benzene. The mixture was refluxed for 2 hours before adding over 20 minutes solid 1-(2-chloroethyl)-4-benzamidopiperidine (1.33 g., 0.005 mole). Refluxing was continued for 6½ hours before cooling and filtering. To the filtrate was added petroleum ether (b.p. 60°–80°) and on standing at 0° for 24 hours a yellow solid (585 mg.) was precipitated and filtered off. The mother liquor was evaporated to give a residue which gave 830 mg. of almost pure title compound (m.p. 129.7° C) after washing in ether. A recrystallisation from aqueous methanol gave the title compound as its hemihydrate, m.p. 134.2° C. [$C_{27}H_{32}N_4O_2.\frac{1}{2}H_2O$ requires C, 71.48; H, 7.33; N, 12.35%. Found: C, 71.85; H, 7.23; N, 12.34%].

EXAMPLE 12 a. 1-(3-Chloropropyl)-4-(2-methylbenzamido)piperidine

The title compound is prepared in a similar manner to Example 1(a) and (b) using 4-(2-methylbenzamido)-piperidine and 3-bromopropanol as starting materials in part (a).

b. 1-[3-(N-benzyl-N-2-pyridyl amino)propyl]-4-(2-methylbenzamido)piperidine

The title compound is prepared in a similar manner to Example 11 from 1-(3-chloropropyl)-4-(2-methylbenzamido)piperidine and 2-(benzylamino)pyridine.

EXAMPLE 13 a. 1-(2-Chloroethyl)-4-(2,6-dichlorobenzamido)piperidine

The title compound is prepared in a manner similar to Example 1(a) and (b) using 4-(2,6-dichlorobenzamido) piperidine instead of 4-benzamidopiperidine.

b. 4-(2,6-Dichlorobenzamido)-1-(2-[N-(p-methylbenzyl)-N-(2-pyridyl)amino]ethyl)piperidine The title compound is prepared in a manner similar to Example 11 using 1-(2-chloroethyl)-4-(2,6-dichlorobenzamido)piperidine and 2-(p-methylbenzyl)aminopyridine.

EXAMPLE 14 a. 1-(2-Chloroethyl)-4-(p-nitrobenzamido)piperidine

The title compound is prepared in a similar manner to Example 1(a) and (b) using 4-(p-nitrobenzamido)piperidine instead of 4-benzamidopiperidine.

b. 1-(2-[N-(p-Chlorobenzyl)-N-(2-pyridyl) amino]ethyl)-4-(p-nitrobenzamido)piperidine The title compound is prepared in a manner similar to Example 11 using 1-(2-chloroethyl)-4-(p-nitrobenzamido)piperidine and 2-(p-chlorobenzyl)aminopyridine. The compounds having formula I can be processed into pharmaceutical compositions in known manner. The formation of such a composition is illustrated by the following Example.

EXAMPLE 15

The ingredients per tablet are

| | |
|---|---:|
| 4-Benzamido-1-(3-phenylhydrazobutyl)piperidine hydrochloride | 55.25 mg. |
| Avicel pH 101 (microcrystalline cellulose) | 108 mg. |
| Amberlite IRP 88 (an ion exchange resin) | 7 mg. |
| Lactose B.P. | 178.8 mg. |
| Magnesium stearate | 0.9 mg. |

The ingredients are sieved and mixed together and compressed into tablets.

What is claimed is:

1. A pharmaceutical composition having hypotensive activity or central nervous system activity comprising a carrier and an effective amount of a compound selected from those of the formula

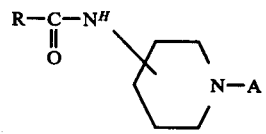

and their pharmaceutically acceptable acid addition salts, wherein A represents a member selected from the class consisting of
   i. alkyl containing 2 to 3 carbon atoms monosubstituted by a substituent selected from hydroxyl, di(-lower alkyl) amino, cyano, halogen, groups of the formula -CO.NX.Y where X and Y are selected from hydrogen and lower alkyl, groups of the formula -CO.T where T is lower alkyl, the semicarbazone and phenylhydrazone derivatives of said groups of formula -CO.T, (Lower alkoxy) carbonyl and groups of the formula -N(CH$_2$R$^1$)R$^2$ where R$^1$ is selected from phenyl, monohalophenyl, mono(lower alkyl) phenyl and mono (lower alkoxy) phenyl and R$^2$ is pyridyl; and
   ii. di(lower alkyl) amino (lower alkoxy) carbonyl; and R represents a member selected from the class consisting of phenyl and phenyl substituted by one to two substituents selected from lower alkyl, halogen and nitro.

2. A composition according to claim 1, where A represents alkyl containing 2 to 3 carbon atoms mono-substituted by a substituent selected from the class consisting of groups of the formula —N(CH$_2$R$^1$)R where R$^1$ and R$^2$ are as defined in claim 1 and (2) groups of the formula —C(=—NH.C$_6$H$_5$) T where T is lower alkyl.

3. A method of treating hypertension or central nervous system abnormalities in an afflicted mammal, which comprises administering to said mammal an effective amount of a pharmaceutical composition as defined in claim 1.

* * * * *

UNITED STATES PATENT AND TRADEMARK OFFICE
CERTIFICATE OF CORRECTION

PATENT NO. : 4,061,758
DATED : December 6, 1977
INVENTOR(S) : John Leheup Archibald It is certified that error appears in the above-identified patent and that said Letters Patent are hereby corrected as shown below:

Column 3, line 24; "( i )" should be --( I )--.

Column 6, line 28; "phasgene" should be --phosgene--.

Claim 1, line 11 after the formula; " (Lower" should be --(lower--.

Claim 2, line 4; " $-N(CH_2R^1)R$" should be -- $-N(CH_2R^1)R^2$--.

Claim 2, line 6; " $-C(=-NH.C_6H_5)T$ " should be -- $-C(=N-NH.C_6H_5)T$ --.

Signed and Sealed this

Seventeenth Day of October 1978

[SEAL]

Attest:

RUTH C. MASON
*Attesting Officer*

DONALD W. BANNER
*Commissioner of Patents and Trademarks*